(12) United States Patent
Beeckler et al.

(10) Patent No.: US 10,874,824 B2
(45) Date of Patent: Dec. 29, 2020

(54) HIGH-VOLUME MANUFACTURING OF CATHETERS COMPRISING ELECTRODES HAVING LOW IMPEDANCE AT LOW FREQUENCY

(71) Applicant: BIOSENSE WEBSTER (ISRAEL) LTD., Yokneam (IL)

(72) Inventors: Christopher Thomas Beeckler, Brea, CA (US); Joseph Thomas Keyes, Glendora, CA (US)

(73) Assignee: Biosense Webster (Israel) Ltd., Yokneam (IL)

(*) Notice: Subject to any disclaimer, the term of this patent is extended or adjusted under 35 U.S.C. 154(b) by 165 days.

(21) Appl. No.: 15/786,968

(22) Filed: Oct. 18, 2017

(65) Prior Publication Data

US 2019/0111233 A1    Apr. 18, 2019

(51) Int. Cl.
| | | |
|---|---|---|
| *A61M 25/00* | (2006.01) | |
| *A61B 5/042* | (2006.01) | |
| *A61B 5/00* | (2006.01) | |
| *A61B 5/06* | (2006.01) | |
| *A61B 18/14* | (2006.01) | |
| *A61B 18/00* | (2006.01) | |

(52) U.S. Cl.
CPC ........... *A61M 25/001* (2013.01); *A61B 5/042* (2013.01); *A61B 5/0422* (2013.01); *A61B 5/0538* (2013.01); *A61B 5/6852* (2013.01); *A61M 25/0013* (2013.01); *A61M 25/0015* (2013.01); *A61B 5/062* (2013.01); *A61B 18/1492* (2013.01); *A61B 2018/00839* (2013.01); *A61B 2562/028* (2013.01); *A61B 2562/125* (2013.01)

(58) Field of Classification Search
CPC ................................ A61M 25/00; A61M 5/00
See application file for complete search history.

(56) References Cited

U.S. PATENT DOCUMENTS

| 5,391,199 | A | 2/1995 | Ben-Haim |
| 5,507,725 | A * | 4/1996 | Savage ............ A61M 25/0144 |
| | | | 604/95.04 |
| 6,239,724 | B1 | 5/2001 | Doron et al. |
| 6,332,089 | B1 | 12/2001 | Acker et al. |
| 6,400,976 | B1 | 6/2002 | Champeau |

(Continued)

FOREIGN PATENT DOCUMENTS

| EP | 3 315 087 A1 | 5/2018 |
| WO | WO 96/05768 A1 | 2/1996 |
| WO | WO 97/17892 A1 | 5/1997 |

OTHER PUBLICATIONS

International Search Report dated Jan. 14, 2019, International Application No. PCT/US2018/055125.

*Primary Examiner* — Cachet I Proctor

(57) ABSTRACT

A method for producing a distal-end assembly of a medical device, the method includes disposing a first layer on at least part of a given section among one or more sections of a flexible substrate. At one or more selected locations on the given section, which are to serve as electrodes on the distal-end assembly of the medical device, a second layer is disposed so that, when brought into contact with tissue, the second layer has a reduced impedance for transferring electrical signals to or from the tissue at a predefined frequency range, relative to the first layer. The given section is shaped to form the distal-end assembly.

11 Claims, 4 Drawing Sheets

(56) References Cited

U.S. PATENT DOCUMENTS

| | | | |
|---|---|---|---|
| 6,484,118 B1 | 11/2002 | Govari | |
| 6,618,612 B1 | 9/2003 | Acker et al. | |
| 6,690,963 B2 | 2/2004 | Ben-Haim et al. | |
| 7,780,638 B1 * | 8/2010 | Deniega | A61M 25/007 604/264 |
| 9,226,688 B2 * | 1/2016 | Jacobsen | A61B 5/065 |
| 2002/0065455 A1 | 5/2002 | Ben-Haim et al. | |
| 2003/0120150 A1 | 6/2003 | Govari | |
| 2004/0054287 A1 | 3/2004 | Stephens | |
| 2004/0068178 A1 | 4/2004 | Govari | |
| 2005/0033136 A1 | 2/2005 | Govari et al. | |
| 2009/0143651 A1 | 6/2009 | Kallback et al. | |
| 2009/0171274 A1 * | 7/2009 | Harlev | A61B 5/0422 604/95.04 |
| 2014/0228838 A1 * | 8/2014 | Kirschenman | A61B 5/0422 606/41 |
| 2015/0276651 A1 | 10/2015 | Petisce | |
| 2015/0351652 A1 | 12/2015 | Marecki et al. | |
| 2016/0317094 A1 * | 11/2016 | Byrd | A61B 5/0538 |
| 2017/0049349 A1 | 2/2017 | Sallee et al. | |
| 2018/0110562 A1 * | 4/2018 | Govari | A61B 5/036 |

\* cited by examiner

HIGH-VOLUME MANUFACTURING OF CATHETERS COMPRISING ELECTRODES HAVING LOW IMPEDANCE AT LOW FREQUENCY

FIELD OF THE INVENTION

The present invention relates generally to producing electrodes for use in medical devices, and particularly to methods for mass production of catheter electrodes having controlled impedance.

BACKGROUND OF THE INVENTION

Some medical devices comprise electrodes that are required to have a certain, typically low, level of impedance. Various production techniques of such electrodes are known in the art.

For example, U.S. Pat. No. 6,400,976 describes a method for producing a catheter with thin film electrodes. An electrical lead for sensing electrical activity with a body of a patient and for applying electrical energy to selected body tissue comprises an elongated, flexible polymeric lead body having one or more conductors extending the length thereof. The conductors being connected at their distal end to electrode pads where each of the pads comprise a multi-layer thin metallic film structure formed on the surface of the lead body where the overall thickness of the composite electrodes are less than about 5 microns.

U.S. Patent Application Publication 2015/0276651 describes methods for fabricating analyte sensor components using IC-based or MEMs-based fabrication techniques. Fabrication of the analyte sensor component comprises providing an inorganic substrate having deposited thereon a release layer, a first flexible dielectric layer and a second flexible dielectric layer insulating there between electrodes, contact pads and traces connecting the electrodes and the contact pads of a plurality of sensors. Openings are provided in one of the dielectric layers over one or more of the electrodes to receive an analyte sensing membrane for the detection of an analyte of interest and for electrical connection with external electronics.

SUMMARY OF THE INVENTION

An embodiment of the present invention that is described herein provides a method for producing a distal-end assembly of a medical device, the method includes disposing a first layer on at least part of a given section among one or more sections of a flexible substrate. At one or more selected locations on the given section, which are to serve as electrodes on the distal-end assembly of the medical device, a second layer is disposed so that, when brought into contact with tissue, the second layer has a reduced impedance for transferring electrical signals to or from the tissue at a predefined frequency range, relative to the first layer. The given section is shaped to form the distal-end assembly.

In some embodiments, shaping the given section includes cutting the flexible substrate to separate the given section from one or more neighboring sections. In other embodiments, shaping the given section includes wrapping the given section around a distal end of the medical device. In yet other embodiments, disposing the first layer includes depositing a gold layer on the given section, and patterning the gold layer so as to retain only parts of the gold layer on the at least part of the given section.

In an embodiment, disposing the second layer includes disposing one or more sublayers of materials selected from a list consisting of titanium nitride (TiN), iridium oxide (IrOx), and platinum black. In another embodiment, disposing the second layer at the selected locations includes depositing the second layer on the given section and on the first layer, and patterning the second layer so as to retain only parts of the second layer on the selected locations. In yet another embodiment, disposing the second layer includes depositing the second layer using a physical vapor deposition (PVD) process.

In some embodiments, the medical device includes an insertion tube of a catheter. In other embodiments, the flexible substrate includes a flexible printed circuit board (PCB). In yet other embodiments, the flexible substrate includes electrical interconnections, and disposing the first and second layers includes laying out at least one of the first and second layers to make contact with at least one of the electrical interconnections.

In an embodiment, the method includes perforating the flexible substrate so as to form irrigation holes. In another embodiment, the predefined frequency range includes 0.01 to 1000 Hz.

The present invention will be more fully understood from the following detailed description of the embodiments thereof, taken together with the drawings in which:

DETAILED DESCRIPTION OF EMBODIMENTS

Overview

Figure 1:
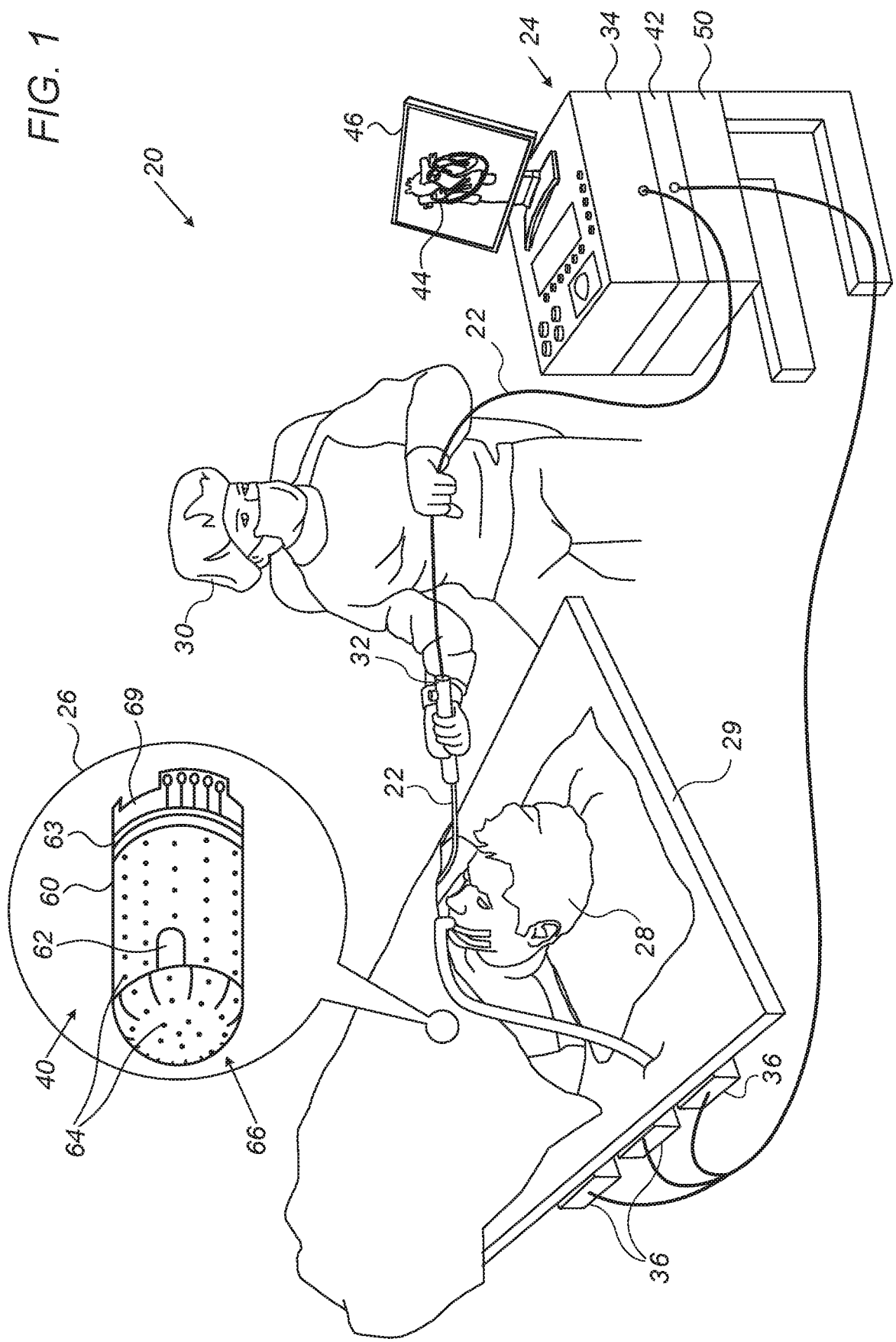
FIG. 1 is a schematic, pictorial illustration of a catheterization system, in accordance with an embodiment of the present invention.

Medical devices such as some types of catheters comprise electrodes that are used, for example, for conducting electrical signals to or from patient tissue. In some cases, the electrodes are required to exhibit low impedance at low frequencies. Electrodes of this sort are useful, for example, for sensing low-amplitude signals, and for reducing noise level associated with the sensed signals.

Embodiments of the present invention that are described hereinbelow provide methods for producing a catheter tip that comprises electrodes having low impedance at low frequencies. In principle, it is possible to produce such electrodes by coating (e.g., soldering or gluing) discrete locations of a catheter with conductive (e.g., metal) layers. These metal layers reduce the impedance of the electrode at low frequencies, but such coating processes are inefficient for high volume manufacturing (HVM). The disclosed techniques enable producing the electrodes at the discrete locations using very large scale integration (VLSI) processes that enable high productivity in HVM.

In some embodiments, a first conductive layer, such as a gold layer, is deposited at predefined locations of a flexible substrate, such as a multi-layered flexible printed circuit board (PCB) sheet, which is provided in a planar form and is configured to wrap around an insertion tube of a catheter.

In some embodiments, a second conductive layer, such as a titanium nitride (TiN), iridium oxide (IrOx), or platinum black layer, is deposited at one or more selected locations on an outer surface of the flexible PCB. In these embodiments, the second conductive layer may be coated on top of the gold layer, or directly on the outer surface of the flexible PCB.

In an embodiment, the deposited layers are metallized, or made from any other suitable material, such as electrically conductive ceramic materials (e.g., TiN or IrOx, or platinum black). In an embodiment, the deposited layers are configured to function as electrodes on a tip of the catheter. In this embodiment, when the electrodes are brought into contact with tissue, the TiN or IrOx, or platinum black layer has a reduced impedance for transferring electrical signals to or from the tissue at a predefined frequency range (e.g., 0.01-1000 Hz), relative to the gold layer.

In some embodiments, the deposition of the first (e.g., gold) and second (e.g., TiN) layers may be carried out using sputtering techniques, such as physical vapor deposition (PVD), followed by patterning the layers to the shape of the electrodes, using masking techniques, such as lithography and etching. In these embodiments, each layer may be implemented using a dedicated respective mask so as to pattern the layers at different locations on the flexible PCB. In cases in which the second layer is patterned at the same locations as the first layer, a single mask may be sufficient.

In some embodiments, the flexible PCB may comprise multiple substantially identical sections, such that each section may be used to produce a separate catheter tip. Note that by using a single PCB sheet to produce multiple catheter tips, the production costs per catheter are reduced. In these embodiments, after producing the electrodes on the PCB sheet, each section is singulated (i.e., decoupled from the other sections) and wrapped around an insertion tube, so as to produce the distal end (e.g., tip) of the catheter.

The disclosed techniques help to increase the functionality of medical catheters by producing them with electrodes having low impedance at low frequencies, without compromising production costs. Furthermore, using VLSI processes on flexible substrates reduce the production cost of the distal end. For example, the disclosed techniques enable controlled level of impedance per electrode using selected materials and patterning masks. The flexible PCB sheet can be wrapped around a low cost molded plastic assembly rather than producing expensive micro-machined metal tubes, so as to further reduce the production costs.

System Description

FIG. 1 is a schematic, pictorial illustration of a catheterization system 20, in accordance with an embodiment of the present invention. System 20 comprises a probe, in the present example a cardiac catheter 22, and a control console 24. In the embodiment described herein, catheter may be used for any suitable therapeutic and/or diagnostic purposes, such as sensing signals from a heart (not shown) of a patient 28.

Console 24 comprises a processor 34, typically a general-purpose computer, with suitable front end and interface circuits for receiving signals from catheter 22 and for controlling the other components of system 20 described herein. In some embodiments, console 24 further comprises a memory 50 and a display 46, configured to display data, such as an image 44 of at least part of the heart of patient 28. In some embodiments, image 44 may be acquired using a computerized tomography (CT) system, by a magnetic resonance imaging (MRI) scanner, or using any other suitable anatomical imaging system.

A physician 30 (such as an interventional cardiologist) inserts catheter 22 through the vascular system of patient 28 lying on a table 29. Catheter 22 comprises a distal-end assembly 40, shown in an inset 26 and depicted in details in FIGS. 2-4. Physician 30 moves assembly 40 in the vicinity of the target region in the heart by manipulating catheter 22 with a manipulator 32 near the proximal end of catheter 22. The proximal end of catheter 22 is connected to interface circuitry in processor 34.

In some embodiments, the position of distal-end assembly 40 in the heart cavity is typically measured using position sensing techniques.

This method of position sensing is implemented, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In some embodiments, console 24 comprises a driver circuit 42, which drives magnetic field generators 36 placed at known positions external to patient 28 lying on table 29, e.g., below the patient's torso.

Reference is now made to inset 26. In some embodiments, distal-end assembly 40 comprises a flexible printed circuit board (PCB) sheet 60, wrapped around an internal member 69 depicted in detail in FIG. 4 below. The internal member is also referred to herein as an insertion tube. In some embodiments, assembly 40 further comprises a dome-cover 66, which is fabricated from a flexible PCB and configured to wrap around a ring-shaped dome-support (shown in FIG. 4 below) using any suitable coupling technique.

In some embodiments, PCB sheet 60 and/or dome-cover 66 may be perforated so as to form one or more irrigation holes 64, which are configured to allow irrigation fluid to flow out from the insertion tube when irrigating the tissue of the heart, for example during an ablation procedure.

In some embodiments, assembly 40 further comprises one or more micro-electrodes 62 and/or one or more ring electrodes 63, which are configured to conduct electrical signals to or from the tissue of the heart. During a medical procedure, such as a cardiac mapping, micro-electrodes 62 and/or ring electrodes 63 are brought into contact with the tissue of the heart, so as to sense electrical signals originated therefrom. In the context of the present disclosure and in the claims, the terms "electrode" and "micro-electrode" are used interchangeably.

In some embodiments, electrodes 62 and 63 are coated with a gold layer (shown in FIG. 3 below) and one or more additional layers, made from titanium nitride (TiN), or iridium oxide (IrOx), or platinum black, or any other suitable materials. These additional layers are configured to transfer from the tissue of the heart, electrical signals at a predefined frequency range (e.g., 0.01-1000 Hz at a reduced impedance relative to the impedance of the gold layer. The reduced impedance at low frequencies is required for sensing low-amplitude electrical signals and for reducing the noise level associated with the sensed signals.

In some embodiments, assembly 40 may be used for ablating tissue of the heart. In some embodiments, during the ablation, micro-electrodes 62 are configured to receive from the tissue electrical signals at the above frequency range, at a reduced impedance relative to the impedance of the gold layer. The reduced impedance enables improved signal quality from the micro-electrodes. Since the surface area of the electrode affects the impedance, lowering the impedance with a coating allows for the design of a smaller micro-electrode with the same impedance properties.

In some embodiments, the gold layer is typically deposited on an outer surface of PCB sheet 60 and/or on dome-cover 66, followed by a deposition of the additional layers, on top of, or instead of the gold layer. The production sequence is depicted in details in FIGS. 2-4 below.

In some embodiments, components such as one or more thermocouples (not shown), may be produced between the layers of PCB sheet 60 or mounted on the outer surface of PCB sheet 60, so as to monitor tissue temperature during the ablation.

In some embodiments, processor 34 typically comprises a general-purpose processor, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The configuration of assembly 40 shown in FIG. 1 is an example configuration, which is chosen purely for the sake of conceptual clarity. In alternative embodiments, any other suitable configuration can also be used. For example, the size and shape of assembly 40, and the number and locations of micro-electrodes 62 and/or ring electrodes 63 may be implemented using any suitable components and layout appropriate for conducting a suitable medical procedure on tissue of any organ of patient 28. Furthermore, the flexible substrate used for implementing the distal-end device may comprise any other suitable substrate, not necessarily a PCB, and any alternative suitable materials may be used in micro-electrodes 62 and in ring electrodes 63.

Figure 2:
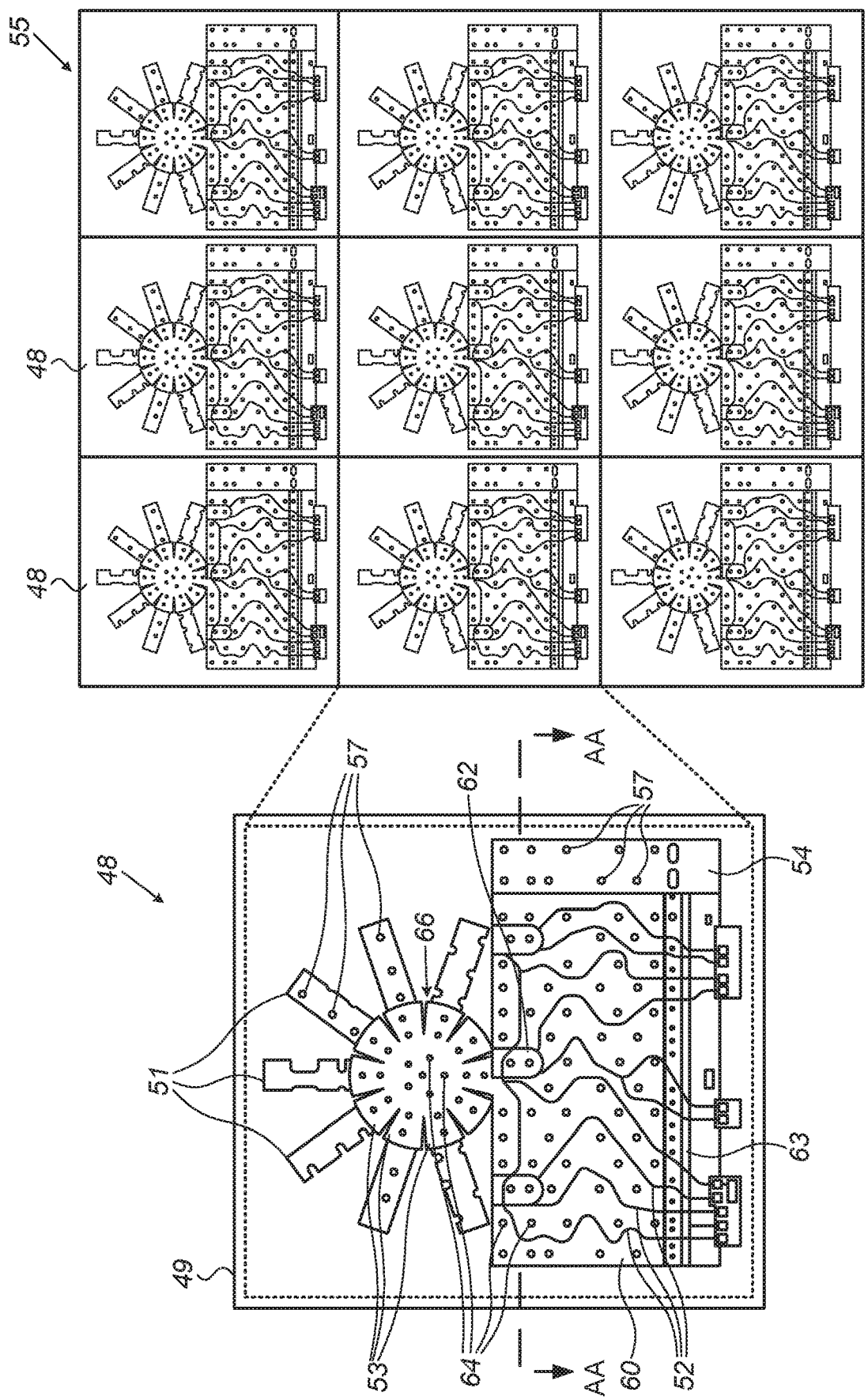
FIG. 2 is a schematic, pictorial illustration of a flexible substrate having electrodes printed thereon, in accordance with an embodiment of the present invention.

High-Volume Manufacturing (HVM) of Catheters Comprising Electrodes Having Low Impedance at Low Frequency FIG. 2 is a schematic, pictorial illustration of a substrate 55 comprising an array of multiple sections 48, in accordance with an embodiment of the present invention.

In some embodiments, substrate 55 may comprise one or more substantially identical sections 48, in the example of FIG. 2 substrate 55 comprises an array of nine sections 48, but in alternative embodiments, substrate 55 may comprise any other suitable number of sections arranged in any suitable layout.

In some embodiments, each section 48 comprises sheet 60, cover 66 and all other elements of assembly 40 depicted in FIG. 1, such that each section 48 may be used for producing a single unit of distal-end assembly 40.

These embodiments enable high-volume manufacturing (HVM) of assemblies 40 by applying on substrate 55 one set of very large scale integration (VLSI) processes, described with reference to FIG. 1 above, for simultaneously producing multiple sections 48. After concluding the production of sections 48, substrate 55 is cut, such that each section 48 is singulated as shown in an inset 49, to which reference is now made.

In some embodiments, PCB sheet 60 typically comprises electrical interconnections, such as conductive traces 52, which are configured to electrically connect the electronic devices coupled to the PCB to suitable wires that traverse the catheter, and to electrically connect between the proximal end of catheter 22 and electrodes 62 and 63.

In an embodiment, irrigation holes are formed in sheet 60 and/or on dome-cover 66, when sheet 60 and cover 66 are in a planar position, before wrapping around member 69 and the ring-shaped dome-support shown in FIG. 4 below.

In some embodiments, sheet 60 comprises a section 54, which is configured to connect the edges of sheet 60 to one another, when sheet 60 is wrapped around member 69, and to connect between sheet 60 and cover 66, as will be described below.

In some embodiments, cover 66 comprises multiple tabs 51, each of which is extended from a respective section 53 of cover 66, and are configured to couple between dome-cover 66 and section 54 of sheet 60.

In some embodiments, section 54 and some of tabs 51 comprise coupling elements 57, which are inserted into intrusions in some of tabs 51 so as to couple between sheet 60 and cover 66 in a wrapped position around member 69.

In alternative embodiments, after wrapping, the left and right edges of sheet 60 may be coupled to one another by an adhesive, welding, or using any other suitable technique to couple sheet 60 and cover 66 to member 69, and to one another.

Figure 3:
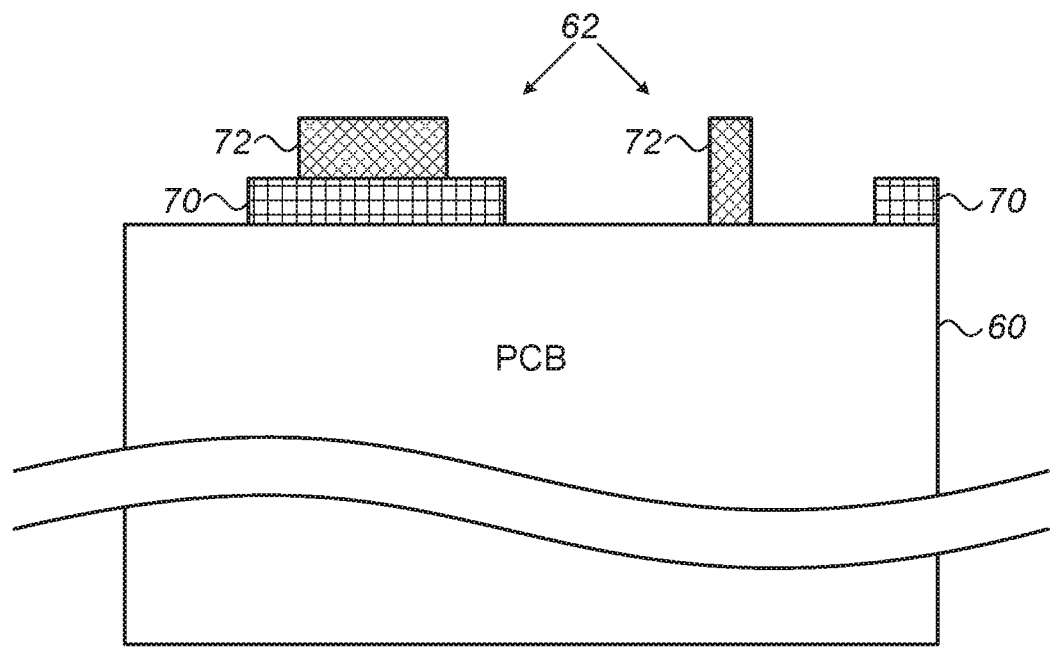
FIG. 3 is a schematic, sectional side view showing micro-electrodes formed on a flexible substrate, in accordance with an embodiment of the present invention.

In some embodiments, sheet 60 and cover 66 of section 48 are shown in a planar form after concluding the VLSI processes, and before wrapping sheet 60 and cover 66 around member 69 and on the apex of assembly 40, respectively, as will be depicted in detail in FIG. 4 below. FIG. 3 below depicts a sectional side view of a section AA shown in FIG. 2.

FIG. 3 is a schematic, sectional side view showing micro-electrodes 62 formed on PCB sheet 60, in accordance with an embodiment of the present invention. In some embodiments, section AA shows two out of three electrodes 62 shown in FIG. 2. In some embodiments, micro-electrode 62 may comprise a TiN layer 72 patterned over a gold layer 70, or a TiN layer patterned directly on PCB sheet 60, as shown in the two exemplary electrodes 62 of FIG. 3.

Furthermore, across sheet 60, the impedance of each electrode may be controlled by setting a respective thickness of the interface material (e.g., increasing the thickness of the TiN to create more effective surface area) of electrode 62.

In some embodiments, all electrodes 62 of a given assembly 40 may share a common layered structure that determines the class of assembly 40 with respect to sensing sensitivity of a predefined range of frequencies. In alternative embodiments, different micro-electrodes 62 in assembly 40 may have different structures of layers.

In some embodiments, the top surface of electrodes 62 is designed to be brought into contact with the tissue of the heart. For example, the top surfaces of electrodes 62 (and of ring electrodes 63) are atraumatic as the height differences of different layer stackups are in the micron range which prevents any damage to the tissue in question.

Figure 4:
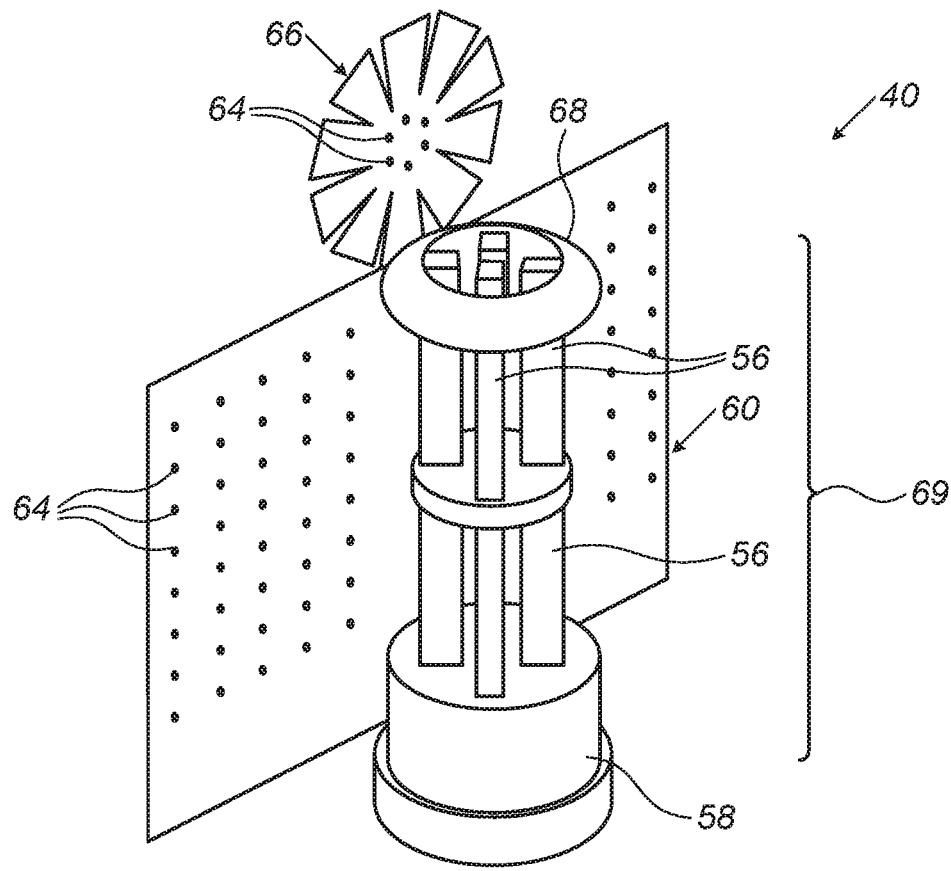
FIG. 4 is a schematic, exploded pictorial illustration of a distal-end assembly of a catheter, in accordance with an embodiment of the present invention.

FIG. 4 is a schematic, exploded pictorial illustration of distal-end assembly 40, in accordance with an embodiment of the present invention. FIG. 4 shows the opposite surfaces of sheet 60 and cover 66 from those shown in FIG. 2.

In some embodiments, internal member 69 of distal-end assembly 40 may be made of plastic or any other suitable material. Member 69 may have a skeleton support structure, as shown in FIG. 4, or any other suitable structure as will be described in other embodiments below.

A base 58 is located at the proximal end of member 69, a ring-shaped dome-support 68 is located at the apex of member 69, and multiple ribs 56 connect the base and the dome-support. In this embodiment, member 69 has an internal lumen for directing irrigation into the inside of cavity formed by flexible PCB sheet 60.

In some embodiments, dome-cover 66 may be glued to dome-support 68. In alternative embodiments, cover 66 may be fabricated from a liquid crystal polymer (LCP) PCB, which may be formed (e.g., thermoformed) into a cup shape and bonded to sheet 60. The cup shape may be bonded to dome-support 68 and sheet 60 bonded to base 58 using any suitable bonding technique known in the art.

In some embodiments, sheet 60 and cover 66 are made from a single piece of contiguous PCB or any other suitable flexible substrate. In alternative embodiments, sheet 60 and cover 66 may be formed from separate pieces of material and coupled to one another using welding or any other suitable coupling technique.

The configuration of layers 70 and 72 shown in FIG. 4 is an example configuration, which is chosen purely for the sake of conceptual clarity. In alternative embodiments, any other suitable configuration can also be used. For example, FIG. 3 does not show traces 52 that are extended from electrodes 62 and 63, as shown in FIG. 2 above. In addition, the sublayers of PCB sheet 60 are not shown in the sectional view of FIG. 3.

Figure 5:
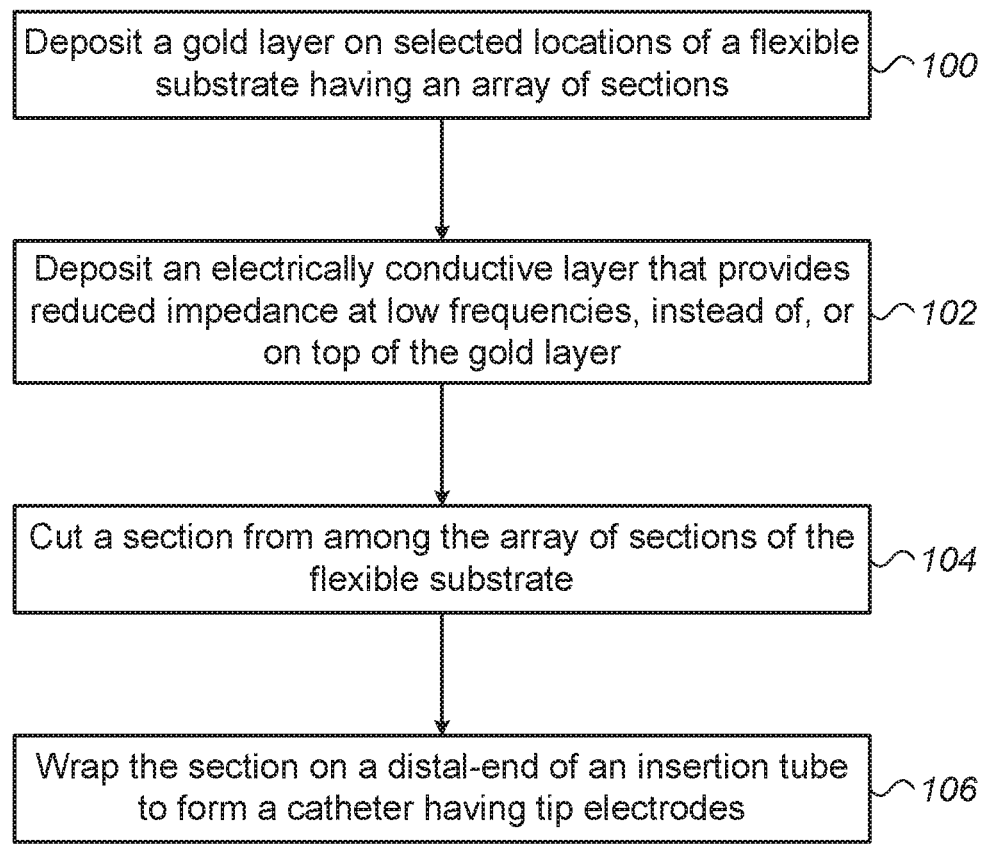
FIG. 5 is a flow chart that schematically illustrates a method for producing a catheter with electrodes having low impedance, in accordance with an embodiment of the present invention.

FIG. 5 is a flow chart that schematically illustrates a method for producing distal-end assembly 40 with electrodes 62 and 63 having low impedance, in accordance with an embodiment of the present invention. The method begins with depositing gold layer 70 on selected locations of substrate 55 having an array of sections 48, at a gold deposition step 100.

In some embodiments, substrate 55 may already be perforated with irrigation holes 64 before conducting step 100. Note that all other elements of sections 48 depicted in FIG. 2 above, excluding micro-electrodes 62 and/or ring electrodes 63, may be formed before or after step 100.

In some embodiments, the deposition may be carried out across the surface of substrate 55, using PVD, electroplating, or any other suitable deposition technique.

In an embodiment, a patterning step (not shown) may be carried out using a lithography mask and etching, or any other suitable patterning technique, so as to define the selected location. The patterning step may be carried out after the deposition, or before the deposition, e.g., by preparing trenches at the selected locations in which gold layer 70 is to be deposited.

Note that using the disclosed techniques, all nine sections 48 are deposited using a single deposition step of gold layer 70, and one patterning cycle (e.g., lithography and etching). In some cases, the lithography mask may comprise less than nine sections 48, so that the patterning step may comprise multiple sub-steps. For example, the mask may comprise three sections 48, in which case, the lithography step comprises three sub-steps, using a step-and-scan scheme or any other suitable lithography technique. When step 100 concludes, gold layer 70 is deposited on selected locations of a surface of sheet 60 and/or cover 66 of all sections 48 of substrate 55.

At a second deposition step 102, a second layer that provides reduced impedance at low frequencies, such as TiN layer 72 or any other suitable material, is deposited on top of gold layer 70. The deposition and patterning of the second layer may be carried out using PVD or any other suitable technique, and the patterning process is carried out in a similar manner to the patterning of gold metal 70, except for process adaptations related to the type of material. For example, the etching chemistry of TiN layer 72 typically differs from the etching chemistry of gold layer 70, and a second mask may be used when employing different respective patterns in producing layers 70 and 72.

The configuration of PCB sheet 60 and layers 70 and 72 is an exemplary simplified configuration, which is chosen purely for the sake of conceptual clarity. In alternative embodiments, any other suitable configuration can also be used.

At a singulation step 104, substrate 55 is cut so that each section 48 is singulated. Note that step 104 is skipped in case substrate 55 comprises a single section 48. In some embodiments, each section 48 may be further patterned, before or after performing step 104. For example, the substrate between tabs 51 and between sections 53 is cut so as to form the final two-dimensional shape of section 48 in a planar position as shown, for example, in FIG. 4 above.

At a tip formation step 106, each section 48 is wrapped around member 69 as depicted in FIG. 4 above. In the example of distal-end assembly 40, flexible PCB sheet 60 is wrapped around base 58 and ribs 56, and dome-cover 66 is wrapped around dome-support 68. Note that step 106 concludes the method and enable the shaping of section 48 so as to form the distal tip of assembly 40.

Although the embodiments described herein mainly address production of catheters used for sensing and treating arrhythmia, the methods and systems described herein can also be used in other applications, such as in production of any medical device having electrodes or micro-electrodes, for instance in otolaryngology or neurology procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for producing a distal-end assembly of a medical device, the method comprising:
disposing a first layer on at least part of a given section among one or more sections of a flexible substrate, the flexible substrate having a dome cover;
at one or more selected locations on the given section, which are to serve as electrodes on the distal-end assembly of the medical device, disposing a second layer that, when brought into contact with tissue, has a reduced impedance for transferring electrical signals to or from the tissue at a predefined frequency range, relative to the first layer; and
shaping the flexible substrate to form the distal-end assembly by providing a base, multiple ribs and a dome with the ribs connected to the base and dome;

wrapping the given section around the base and ribs; and bonding the dome cover to the dome.

2. The method according to claim 1, wherein shaping the given section comprises cutting the flexible substrate to separate the given section from one or more neighboring sections.

3. The method according to claim 1, wherein disposing the first layer comprises depositing a gold layer on the given section and patterning the gold layer so as to retain only parts of the gold layer on the at least part of the given section.

4. The method according to claim 1, wherein disposing the second layer comprises disposing one or more sublayers of materials selected from a list consisting of titanium nitride (TiN), iridium oxide (IrOx), and platinum black.

5. The method according to claim 1, wherein disposing the second layer at the selected locations comprises depositing the second layer on the given section and on the first layer, and patterning the second layer so as to retain only parts of the second layer on the selected locations.

6. The method according to claim 1, wherein disposing the second layer comprises depositing the second layer using a physical vapor deposition (PVD) process.

7. The method according to claim 1, wherein the medical device comprises an insertion tube of a catheter.

8. The method according to claim 1, wherein the flexible substrate comprises a flexible printed circuit board (PCB).

9. The method according to claim 1, wherein the flexible substrate comprises electrical interconnections, and wherein disposing the first and second layers comprises laying out at least one of the first and second layers to make contact with at least one of the electrical interconnections.

10. The method according to claim 1, and comprising perforating the flexible substrate so as to form irrigation holes.

11. The method according to claim 1, wherein the predefined frequency range comprises 0.01 to 1000 Hz.

* * * * *